United States Patent [19]

Usami et al.

[11] 4,289,130
[45] Sep. 15, 1981

[54] ABSORBENT MATERIAL FOR SANITARY PRODUCTS

[75] Inventors: Akira Usami, Sakai; Toshiaki Uebayashi, Himeji; Koji Sato, Kyoto; Tomoko Goda, Kochi, all of Japan

[73] Assignees: Daicel Ltd., Osaka; Fuji Sanitary Industries Co., Ltd., Kochi, both of Japan

[21] Appl. No.: 68,534

[22] Filed: Aug. 21, 1979

[51] Int. Cl.³ .............................................. A61F 13/16
[52] U.S. Cl. .................................. 128/287; 428/284; 428/286; 428/297; 428/298; 428/302; 428/303; 428/397; 428/401; 428/913
[58] Field of Search ............... 428/284, 286, 288, 364, 428/369, 393, 397, 532, 533, 534, 297, 298, 302, 303, 913, 401; 128/285, 287, 290 R, 284

[56] References Cited

U.S. PATENT DOCUMENTS 2,543,101  2/1951  Francis ............................ 156/62.2

FOREIGN PATENT DOCUMENTS 38-24550  7/1963  Japan .
38-13698  11/1963  Japan .
50-19875  7/1975  Japan .

*Primary Examiner*—James J. Bell
*Attorney, Agent, or Firm*—Armstrong, Nikaido, Marmelstein & Kubovcik

[57] ABSTRACT

An absorbent material comprising cellulose acetate fibers has a good capacity to absorb water and a slow speed of water absorption, so that it can be successfully used to make sanitary products such as disposable diapers and sanitary napkins. The sanitary products prepared with the absorbent material provide improved comfortableness and leakproof properties.

11 Claims, 5 Drawing Figures

ABSORBENT MATERIAL FOR SANITARY PRODUCTS

FIELD OF THE INVENTION

This invention relates to an absorbent material for use in sanitary or hygienic products, and more particularly to sanitary products, for example, disposable diapers and sanitary napkins make of an absorbent material comprising predominantly cellulose acetate fibers.

BACKGROUND OF THE INVENTION

Such sanitary products as mentioned above are required to have an ability to absorb liquid excretions from human bodies and besides to have a leakproofness, breathability, comfortable properties in use and easiness of disposal after use. In general, commercially available sanitary products have a multi-layer structure of three or more layers since it is difficult to meet all of the above requirements with a single material. More precisely, as the main constituent elements of commercially available sanitary products, there are following three layers: a covering material layer which is to directly contact with human body, an absorbent material layer which is between the former layer and a liquid excretion-leakproof material layer and serves to absorb and retain therein liquid excretions, and the above mentioned liquid excretion-leakproof material layer.

The absorbent material to be used in sanitary articles must have a great capacity of water absorption and for this reason cellulosic materials such as paper, cotton and pulp have hitherto been used as the absorbent. However, materials of a great absorption capacity generally exhibit a high speed of water absorption. Therefore, if liquid excretions pass through the covering layer and contact the absorbent layer, the latter will rapidly absorb the excretions. The absorption tends to take place very locally with the result that the liquid excretions are usually difficult to be evenly permeated and distributed into the other portions of the absorbent material. The absorbent layer swelled by the local absorption of a large amount of liquid expels the liquid at a time when the external pressure applied thereto changes. This may lead to leakage of the liquid from the sanitary products. The leakage problem may be obviated if the liquid is evenly distributed throughout the absorbent material, however in general the material having a high speed of water absorption is inclined to locally absorb the liquid, which may often give rise to the leakage problem. If the leakproof layer is reinforced to prevent the leakage, the liquid evacuated from the absorbent layer will exude towards human bodies. This phenomenon is so-called "back-permeation" (or "reflux"). The phenomenon inevitably has the greatest influence on comfortableness in use of the product concerned.

In order to solve the above-mentioned problem on sanitary products, attempts have been made to distribute the liquid throughout the absorbent material by using a denser material, for example, paper or pulp fluff, employing a multi-layer structure of several kinds of materials or incorporating a material of a slow permeation speed into the absorbent layer. In general, however, a material of a lower permeation speed has a smaller water absorption, and a denser material is less flexible and increases a whole thickness or loading of the absorbent layer, which is disadvantageous in cost and comfortableness during use.

We have closely studies to avoid the drawbacks of the known products as stated above and discovered the unknown characteristics of cellulose acetate fibers. By taking advantage of the characteristics we have now succeeded in making sanitary products which have improved functions and feelings in use over the conventional products.

An object of this invention is to provide an absorbent material comprising cellulose acetate fibers and being used to make sanitary products.

Another object of the invention is to provide sanitary products, for example, disposable diapers and sanitary napkins, comprising the absorbent material.

Other objects and advantages of the invention will become apparent from the following descriptions.

SUMMARY OF THE INVENTION

According to this invention, there is provided an absorbent material for use in sanitary products comprising cellulose acetate fibers alone or in combination with cellulose fibers.

DETAILED DESCRIPTION OF THE INVENTION

Cellulose acetate fibers are generally appreciated as hydrophobic fibers and to have a lower water content in equilibrium with moisture in atmosphere and not higher speed of water absorption. It has been found, however, that cellulose acetate fibers of crimped filament tow opened homogeneously or of staple fiber web possess an unexpectedly great capacity to absorb and retain water.

In this invention cellulose acetate fibers which the absorbent material comprises can be used in the form of either uniformly opened filament bundle or non-woven fabric web of staple fibers. Where the acetate fibers are used in the form of staple fibers, they may be mixed with cellulose fibers and formed into a mixed web. The cellulose acetate fibers in the form of staple fibers which may be used in the invention include those recovered from filter rods for cigarettes.

Cellulose acetate fibers may be produced by dry spinning, wherein the filament denier and shape of the cross-section of the fibers produced may vary depending upon the shape of a spinneret and the spinning conditions employed. It has been found that the fibers of odd-shaped (not regular) cross section, for example, of X-, Y- or I-shaped cross section have a greater capacity of water absorption than that of common fibers of regular cross section and hence are more suitable to constitute the absorbent material. In particular, we prefer to use the fibers of Y-shaped cross section. With respect to the filament denier, finer fibers have a greater capacity of water absorption. It has been observed, unexpectedly, that the cellulose acetate fibers having a filament denier of not more than 8 deniers possess a water absorption capacity comparable to that of cellulose fibers.

On the other hand, it has been found that the acetate fibers have a lower speed of water absorption than that of cellulose fibers. We have further found that if an oil or plasticizer is applied to the acetate fibers, the absorption speed thereof becomes much lower and that the treatment with such oil or plasticizer unexpectedly has little influence on the absorption capacity of the fibers.

As already stated, the cellulose acetate fibers may constitute the absorbent material of the invention, alone or in combination with cellulose fibers. Where the acetate fibers are combined with cellulose fibers, the latter may be used in an amount up to 900 parts by weight per 100 parts by weight of acetate fibers.

In an embodiment of this invention, the absorbent material may have a two-layer structure consisting of a layer made of cellulose acetate fibers alone or in admixture with cellulose fibers which is to be on the human body side and a layer made of cellulose fibers. The assembly so constructed is advantageous in that the layer of cellulose fibers acts as a main absorber and retainer for liquid excretions concerned, while the layer of acetate fibers serves as both an auxiliary absorber and a back-permeation inhibitor. Further advantage of the acetate fibers is to display a satisfactory impact resilience in response to variation of external pressure for a short time, which imparts better comfortableness in use to sanitary articles.

The cellulose fibers which may be used in the invention include natural fibers (which are preferably used), for example, cotton, wood pulp and the like and regenerated fibers, for example, viscose rayon and cuprammonium rayon.

As already mentioned, fibers recovered from filter rods for cigarettes can be conveniently used as the cellulose acetate fibers. The term "filter rods" used herein means those manufactured from tow of cellulose acetate fibers and includes rejects and wastages resulted from the process of manufacturing filter rods in a factory managed hygenically. Filter tips attached to cigarettes are obtained by cutting the filter rods.

A strict quality standard is regulated for the manufacture of the filter rods, leading to inevitable occurrance of some rejects and wastages during the process. Most of rejects and wastages occur due to inconsistent adhesion of wrapping paper. It is suggested that only the fibers are recovered from the rejects and wastages and envisaged for re-use in different applications, but a majority of the rejects and wastages are actually incinerated and discarded. However, incineration of the waste rods is time- and labor-consuming and uneconomical as they have a small bulk density. Thus, it is very beneficial to utilize such rejects and wastages of filter rods, which is also one of the objects of this invention.

The performance of the cellulose acetate fibers to be used in this invention is illustrated by the following tests.

Test A

In order to evaluate the behavior of staple fibers of various fibers toward water, tests were conducted on water absorption and speed of water absorption of the fibers. Water absorption was determined following the test procedure for water absorption specified with respect to "absorbent cotton" in Pharmacopoeia of Japan. It corresponds to a maximum water quantity to be absorbed in 5 g of the fibers under test.

Speed of water absorption was determined following the test procedure for sedimentation rate specified with regard to "absorbent cotton" in Pharmacopoeia of Japan. A lower value of sedimentation rate indicates a higher speed of water absorption.

The test results are set out in Table 1 below, where symbols "O.T", "N.O.", "T.O." and "P.C." mean application to the fibers of, respectively, "an oil for cigarette filter", "no oil", "a textile oil" and "a plasticizer".

TABLE 1

| No. | Specimen Fresh or recovered material | Filament denier | Shape of cross-section | Symbol | Sedimentation rate (sec) | Water absorption (g) |
|---|---|---|---|---|---|---|
| 1 | Fresh acetate | 9d | Regular | O.T. | 6.5 | 106 |
| 2 | Fresh acetate | 2d | " | " | 6.5 | 148 |
| 3 | Fresh acetate | 8d | Y | N.O. | 6.8 | 142 |
| 4 | Fresh acetate | 4d | Y | " | 6.7 | 154 |
| 5 | Fresh acetate | 2.5d | Y | " | 7.9 | 166 |
| 6 | Fresh acetate | 3.5d | I | T.O. | 22.0 | 159 |
| 7 | Fresh acetate | 8d | Y | O.T. | 5.8 | 144 |
| 8 | Fresh acetate | 8d | Y | T.O. | 20.2 | 144 |
| 9 | Recovered waste rods | 2.5d | Y | P.C. | 15.3 | 103 |
| 10 | Recovered waste rods | 4d | Y | P.C. | 30.4 | 98 |
| 11 | Absorbent cotton of Pharmacopoeis of Japan | | | | 4.0 | 119 |
| 12 | Pulp fluff (imported product) | | | | 4.3 | 108 |
| 13 | Pulp fluff ("Taio White" made by Taio Seishi Co.) | | | | 4.6 | 110 |

Specimen No. 9 and Specimen No. 10 consist of fibers recovered from waste rods opened by a cotton carding machine, which contain a few percent by weight of fragments of rod-wrapping paper. The fibers further contain the whole plasticizer which has been applied to acetate fibers in the process of filter-making. Specimen No. 12 and Specimen No. 13 are appreciated in the art to be of best quality as absorbent material for sanitary articles.

The above results shown in Table 1 reveal that the acetate fibers to be used in the invention possess a water absorption equivalent to or higher than that of the known conventional absorbent materials but exhibit a lower speed of water absorption. This shows that the acetate fibers give rise to no local absorption of liquid and enable the absorbed liquid to be evenly distributed throughout the absorbent material.

Test B

The waste rods to be tested were prepared by opening waste rods for cigarette filters by means of a cotton carding machine and removing part of fragments of rod-wrapping paper from the opened waste rods. The waste rods so obtained were mixed with absorbent cotton of Pharmacopoeia in varying proportions and the mixtures were again passed through a cotton carding machine to give webs of the mixed fibers. Ther properties of these webs were determined following the test procedure specified with respect to absorbent cotton by Pharmacopoeia of Japan. The test results are tabulated in Table 2 below.

The results show that combination of the waste rods and absorbent cotton gives webs having a great water absorption and a controllable speed of water absorption.

TABLE 2

| | Standard of Pharmacopoeia (Absorbent Cotton) | Specimens (Parts by weight of waste rod/absorbent cotton) | | | | | | |
|---|---|---|---|---|---|---|---|---|
| | | 100/0 | 90/10 | 75/25 | 50/50 | 30/70 | 10/90 | 0/100 |
| Acid & alkali | Not detectable | Not detected | Not detected | Not detected | Not detected | Not detected | Not detected | Not detected |
| Fluorescent brightener | " | Not detected | Not detected | Not detected | Not detected | Not detected | Not detected | Not detected |
| Dyestuff | " | Not detected | Not detected | Not detected | Not detected | Not detected | Not detected | Not detected |
| Water-soluble substance (mg) | <140 | 93.3 | 75.0 | 27.1 | 34.7 | 15.5 | 9.5 | 9.3 |
| Sedimentation rate (sec) | <8 | 27.0 | 21.2 | 13.1 | 8.2 | 6.9 | 4.8 | 3.7 |
| Water absorption (g) | >100 | 114.6 | 113.1 | 111.6 | 116.9 | 125.1 | 125.4 | 123.1 |
| Ash content (%) | <0.25 | 2.60 | 2.25 | 0.91 | 0.99 | 0.39 | 0.26 | 0.11 |

In above Table 2 the results on water-soluble substance and ash content are indicated for reference, although they are not regulated in the applications of disposable diapers and sanitary napkins. In view of the above test results it is believed that sanitary products obtained with the waste rods are hygienically harmless.

Test C

The same tests as described in Test B were conducted except that absorbent cotton was replaced by refined rayon pulp (commercially available under a trade mark "Rayocord" XP from ITT Rayonier Inc.). The results obtained are listed in Table 3 below. For comparison the results obtained with pulp fluff ("Taio White" made by Taio Seishi Co.) are also shown.

TABLE 3

| | Standard of Pharmacopoeia (Absorbent cotton) | Specimens (Parts by weight of waste rod/pulp) | | | | | | Taio White Control |
|---|---|---|---|---|---|---|---|---|
| | | 100/0 | 90/10 | 75/25 | 50/50 | 30/70 | 10/90 | |
| Acid & alkali | Not detectable | Not detected | Not detected | Not detected | Not detected | Not detected | Not detected | Not detected |
| Fluorescent brightener | " | Not detected | Not detected | Not detected | Not detected | Not detected | Not detected | Not detected |
| Dyestuff | " | Not detected | Not detected | Not detected | Not detected | Not detected | Not detected | Not detected |
| Water-soluble substance (mg) | <140 | 93.3 | 86.5 | 84.5 | 51.5 | 36.9 | 25.2 | 24.3 |
| Sedimentation rate (sec) | <8 | 27.0 | 20.3 | 12.2 | 10.0 | 7.5 | 5.6 | 4.6 |
| Water absorption (g) | >100 | 114.6 | 112.0 | 109.3 | 116.3 | 111.8 | 115.0 | 104.1 |
| Ash content (%) | <0.25 | 2.60 | 2.30 | 2.21 | 1.67 | 1.14 | 0.61 | 0.24 |

As is clearly seen from the results of Tests A–C, the cellulose acetate fibers alone or in combination with cellulose fibers are highly advantageous in many respects to make an absorbent material for sanitary products over known conventional fiberous materials used for the same purpose. Further, it is evident that the cellulose acetate fibers recovered from waste rods for cigarette filters can be effectively employed in this invention.

The cellulose acetate fibers can be used in the presence or absence of plasticizers and oils. If plasticizers or oils are present, they must, of course, be non-toxic to human beings.

BRIEF DESCRIPTION OF THE DRAWINGS

The accompanying drawings show some embodiments of the application of the absorbent material according to this invention to sanitary products. Of the drawings.

PREFERRED EMBODIMENTS OF THE INVENTION

This invention is further illustrated but not limited by the following Examples.

EXAMPLE 1

Figure 1:
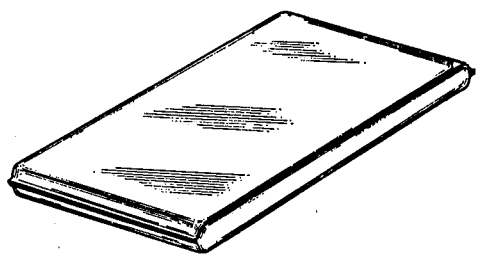
FIG. 1 is a perspective view of a disposable diaper prepared with the absorbent material comprising cellulose acetate fibers.
Figure 2:
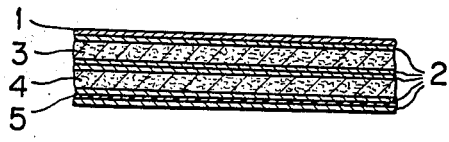
FIG. 2 is a partly cutaway cross-section of the diaper of FIG. 1 to illustrate the multi-layer structure of the diaper.
Figure 3:
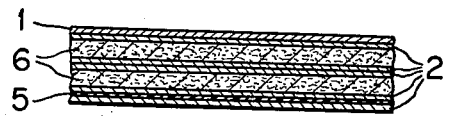
FIG. 3 is a partly cutaway cross-section of another disposable diaper fabricated with the absorbent material consisting of cellulose acetate fibers and cellulose fibers according to the invention.

A disposable diaper for old man having the shape indicated in FIG. 1 and the multi-layer structure as shown in FIG. 2 was made by superimposing non-woven fabric layer 1 of dry-spun polyester/rayon fibers blend, non-woven fabric layer 2 of wet-spun rayon fiber, pulp fluff layer 3, fluff layer 4 of cellulose acetate fibers recovered from waste rods and polyethylene film layer 5. The diaper is referred to as specimen A. Another disposable diaper (referred to as specimen B) for old man of the same shape and having the multi-layer structure as shown in FIG. 3 was fabricated by superimposing layers 1 and 2 of the same materials as above, layer 6 of pulp fluff mixed with 20% by weight of cellulose acetate fibers recovered from waste rods and polyethylene film layer 5. By way of comparison, a commercially available diaper of paper (referred to as specimen C) having the same structure as of specimens A and B but being free from cellulose acetate fibers was ready for use.

Specimens A, B and C (each 65 cm×29 cm dimensions) were put on by old men to make trials of wearing. The performance of each specimen was assessed by the old men and their nurses. All of them stated that specimens A and B were superior to specimen C in respect of both comfortableness in use and leakproofness.

An old woman being sick in bed evaluated that specimens A and B had a cushioning effect of relieving the waist pain due to so called "bed-sore".

EXAMPLE 2

Figure 4:
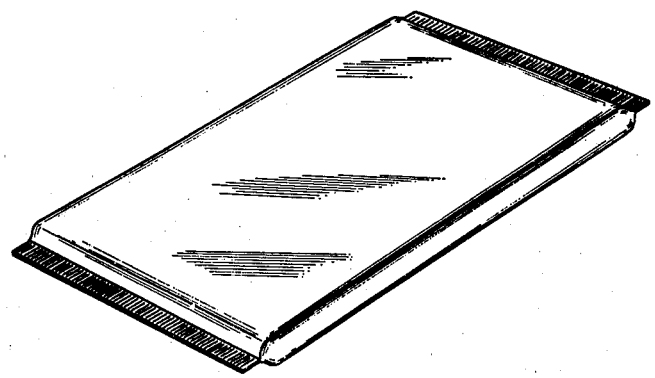
FIG. 4 is a perspective view of a sanitary napkin prepared with the absorbent material according to the invention.
Figure 5:
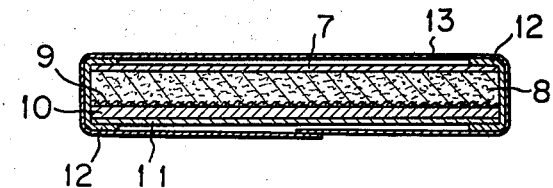
FIG. 5 is a cross-section of the sanitary napkin of FIG. 4.

Sanitary napkins having the multi-layer structure as shown in FIG. 5 were fabricated using the absorbent material of this invention. The multi-layer structure was formed by superimposing in sequence from the human body side, crepe paper layer 7, pulp fluff layer 8, layer 9 of cellulose acetate fibers, leakproof layer 10 of polyethylene film-laminated paper and waterproof paper 11. The structure was provided at the sides with waterproof paper 12. The assembly thus formed was covered with rayon paper 13 laminated with non-woven cotton fabric and then sealed at the longitudinal edges as diagrammatically shown in FIG. 4. The dimensions of the napkin so obtained was 75 mm×185 mm (inclusive of sealed portions) or 75×160 mm (exclusive of sealed portions). The cellulose acetate fibers used were constituted by opened and bank-like extended tow of filament yarns having a filament denier of 1.7 d, a total denier of 43,000 D and the Y-shaped cross section (for speciman No. 1 indicated in Table 4 below) and that of filament yarns having a filament denier of 2.5 d, a total denier of 43,500 D and the Y-shaped cross section (for specimen No. 2 indicated in Table 4). The napkin had a total weight of approx. 6 g.

The napkins prepared as above were subjected to exudation test according to the test procedure for sanitary articles based on Notification No. 14 of the Ministry of Walfare. The test procedure is as follows:

On a filter paper mounted on a glass plate is placed the test specimen of the napkin in such a manner that the available surface (surface to touch a human body) is upwardly disposed. Ten cc of Congo Red solution is dropped over one minute onto the center portion of the specimen and the latter is allowed to stand for one minute. Then, a weight of 1 kg and 50 mm in diameter is imposed on said center portion to observe the exudation of the Congo Red solution from the specimen. If no exudation is observed within 3 minutes after imposition of the weight, the specimen is regarded to meet the standard.

In this test, the weight of 1 kg was replaced by that of 3 kg to make the conditions severer. The test results revealed that both specimen No. 1 (with the acetate fibers of 1.7 d filament denier) and specimen No. 2 (with the acetate fibers of 2.5 d filament denier) satisfied the standard.

Table 4 shows the weight of each of the layers constituting the specimen napkins together with the distributed absorption of each layer for 10 cc Congo Red solution.

TABLE 4

| Constitutional layer | Weight (g) | Distribution absorption (%) | |
|---|---|---|---|
| | | Specimen No. 1 | Specimen No. 2 |
| Rayon paper | 0.672 | 2.0 | 1.8 |
| Non-woven cotton fabric | 0.819 | 2.8 | 4.9 |
| Crepe paper | 0.239 | 5.5 | 4.5 |
| Pulp fluff | 1.940 | 61.8 | 62.2 |
| Acetate fibers | 1.071 (No.1) 1.464 (No.2) | 27.3 | 25.6 |
| Polyethylene film-laminated paper | 0.217 | 0.3 | 0.4 |
| Waterproof paper (bottom face) | 0.324 | 0.1 | 0.1 |
| Waterproof paper (side face × 2) | 0.341 | 0.4 | 0.4 |

EXAMPLE 3

Sanitary napkins having a size and structure similar to those described in Example 2 were prepared. For the purpose of comparison, a napkin of conventional type (Specimen No. 3) was made by superimposing, in sequence from the human body side, crepe paper, first mild waterproof paper, pulp fluff, second mild waterproof paper, water-absorbent paper (8 multi-layers), polyethylene film-laminated paper and waterproof paper, with the side faces of waterproof paper. The pulp fluff and the second mild waterproof paper were replaced by cellulose acetate fibers to make specimen No. 4 and No. 5. The cellulose acetate fibers used were prepared by opening (for specimen No. 4) or not opening (for specimen No. 5), uniformly extending into the band form and cutting filament tow having the Y-shaped cross section, a monofilament denier of 1.7 denier and a total denier of 43,000 denier.

These specimens were subjected to the exudation test as mentioned in Example 2, and the test results showed that each of them satisfied the standard. The results of distributed absorption for 10 cc Congo Red solution are set out in Table 5.

TABLE 5

| Constitutional layer | Weight (g) | Distribution absorption (%) | | |
|---|---|---|---|---|
| | | Specimen No. 3 | No. 4 | No. 5 |
| Crepe paper | 0.715 | 0.3 | 0 | 1.1 |
| Mild waterproof paper | 0.209 | 2.5 | 1.6 | 2.7 |
| Pulp fluff | 1.552 | 18.4 | | |
| Mild waterproof paper | 0.209 | 5.0 | | |
| Cellulose acetate fibers | 1.205 (No.4) 1.987 (No.5) | | 14.8 | 27.1 |
| Water-absorbent paper | 2.044 | 73.5 | 83.2 | 68.7 |
| Polyethylene film-laminated paper | 0.254 | 0.1 | 0 | 0.1 |
| Waterproof paper (bottom face) | 0.448 | 0 | 0 | 0 |
| Waterproof paper (side face × 2) | 0.382 | 0.2 | 0.3 | 0.4 |

What we claim is:

1. In a sanitary product having a multilayered structure comprising a covering layer suitable for contact with the human body, a liquid excretion-leakproof layer and an absorbent layer interposed between the covering layer and the liquid excretion-leakproof layer, the improvement comprising employing as the absorbent layer, a layer of cellulose acetate fibers or a mixture of cellulose acetate fibers and cellulose fibers, the cellulose acetate fibers having an irregular cross-section and having a filament denier of less than 8 deniers.

2. The sanitary product according to claim 1, comprising about 100 parts by weight of cellulose acetate fibers and about 900 to 0 parts by weight of cellulose fibers.

3. The sanitary product according to claim 1, in which the cellulose acetate fibers consist of crimped filament tow opened homogeneously.

4. The sanitary product according to claim 1, in which the acetate fibers consist of web of staple fibers.

5. The sanitary product according to claim 1, in which the acetate fibers have Y-shaped cross section.

6. The sanitary product according to claim 1, in which the acetate fibers consist of fibers recovered from filter rods for cigarette filters.

7. The sanitary product according to claim 1, comprising mixed webs of staple acetate fibers and cellulose fibers.

8. The sanitary product according to claim 1, comprising a multi-layer structure of a layer of the acetate fibers and a layer of the cellulose fibers.

9. A sanitary product according to claim 1 which is a disposable diaper.

10. A sanitary product according to claim 1 which is a sanitary napkin.

11. In a sanitary product having a multilayered structure comprising a covering layer suitable for contact with the human body, a liquid excretion-leakproof layer and an absorbent layer interposed between the covering layer and the liquid excretion-leakproof layer, the improvement wherein the absorbent layer is a plurality of layers, at least one of which consists of cellulose acetate fibers, the cellulose acetate fibers having an irregular cross-section and having a filament denier of less than 8 deniers.

* * * * *